United States Patent [19]

Gleason et al.

[11] Patent Number: 4,533,747

[45] Date of Patent: Aug. 6, 1985

[54] LEUKOTRIENE ANTAGONISTS INTERMEDIATES

[75] Inventors: John G. Gleason, Delran; Ralph F. Hall, Robbinsville, both of N.J.; Thomas W. Ku, Dresher, Pa.

[73] Assignee: SmithKline Beckman Corporation, Philadelphia, Pa.

[21] Appl. No.: 472,772

[22] Filed: Mar. 7, 1983

[51] Int. Cl.$^3$ .................. C07C 149/20; C07C 149/23; A61K 31/16; A61K 31/185
[52] U.S. Cl. .................................... 560/152; 514/826; 560/153; 562/556; 562/557; 562/581; 562/594; 564/153; 564/154; 564/198; 564/199; 564/201
[58] Field of Search ................ 560/152, 153; 564/154, 564/199, 153

[56] References Cited

U.S. PATENT DOCUMENTS 3,873,624 3/1975 Mathew et al. ...................... 560/153
4,130,713 12/1978 Baggiolini et al. .................. 560/153
4,177,277 12/1979 Ondetti et al. ...................... 560/153

*Primary Examiner*—Natalie Trousof
*Assistant Examiner*—Paricia M. Scott
*Attorney, Agent, or Firm*—Richard D. Foggio; Alan D. Lourie

[57] ABSTRACT

The compounds represented by the formula (I)

$$\text{CH}_3(\text{CH}_2)_p \underset{H}{\overset{}{\diagdown}} \text{C}=\text{C} \underset{H}{\overset{\text{CHCHO}}{\diagup}} \quad \overset{\text{S(CH}_2)_m\text{CHCOR}_2'}{\underset{}{|}}\overset{R_1'}{|} \quad (I)$$

wherein m is 0, 1 or 2; p is 9, 10, 11, 12 or 13; $R_1'$ is hydrogen, $$-\text{NHCCF}_3 \overset{\text{O}}{\underset{}{\|}} \text{ or } -\text{NHCCH}_3 \overset{\text{O}}{\underset{}{\|}}$$

and $R_2'$ is amino, $-\text{NHCH}_2\text{CO}_2R_3'$, $$-\underset{\text{CH}_3}{\overset{|}{\text{N}}}\text{CH}_2\text{CO}_2R_3', \quad -\underset{\text{CH}_3}{\overset{|}{\text{NHCHCO}_2R_3'}}, \quad -\underset{\text{CH}(\text{CH}_3)_2}{\overset{|}{\text{NHCHCO}_2R_3'}},$$

$-\text{NHCH}_2\text{CONH}_2$ or $-\text{OR}_3'$ wherein $R_3'$ is an alkyl radical containing one to six carbon atoms with the proviso that when m is 0, $R_1'$ is hydrogen are chemical intermediates in the synthesis of leukotriene antagonists of the formula (II)

$$\text{CH}_3(\text{CH}_2)_p \underset{H}{\overset{}{\diagdown}} \text{C}=\text{C} \underset{H}{\overset{\text{CH—X}}{\diagup}} \quad \overset{\text{S(CH}_2)_m\text{CHCOR}_2}{\underset{}{|}}\overset{R_1}{|} \quad (II)$$

wherein m and p, are described above and $R_1$ is hydrogen, amino or $$-\text{NHCCH}_3; \overset{\text{O}}{\underset{}{\|}}$$

$R_2$ is hydroxyl, amino, $-\text{NHCH}_2\text{CO}_2\text{H}$, $$-\underset{\text{CH}_3}{\overset{|}{\text{N}}}\text{CH}_2\text{CO}_2\text{H}, \quad -\underset{\text{CH}_3}{\overset{|}{\text{NHCHCO}_2\text{H}}}, \quad -\underset{\text{CH}(\text{CH}_3)_2}{\overset{|}{\text{NHCHCO}_2\text{H}}}$$

$-\text{NHCH}_2\text{CONH}_2$; and X is $$-\underset{\text{OH}}{\overset{|}{\text{CHCH}_2\text{CO}_2\text{H}}},$$

$-\text{CO}_2\text{H}$ or $-\text{CH}_2\text{OH}$ which are useful in the treatment of diseases in which leukotrienes are a factor, such as asthma.

3 Claims, No Drawings

LEUKOTRIENE ANTAGONISTS INTERMEDIATES

BACKGROUND OF THE INVENTION

"Slow Reacting Substance of Anaphylaxis" (SRS-A) has been shown to be a highly potent broncho-constricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of cardiovascular effects of histamine.

The discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$ ($LTC_4$), leukotriene-$D_4$, ($LTD_4$) and leukotriene-$E_4$, ($LTE_4$); the structural formulae of which are represented below.

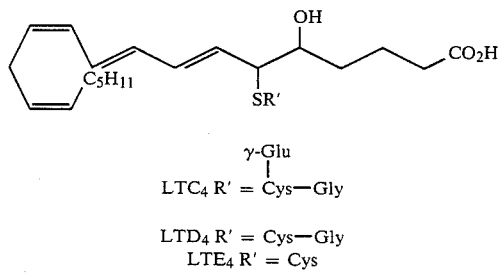

$$\gamma\text{-Glu}$$
$$LTC_4\ R' = Cys\text{—}Gly$$

$$LTD_4\ R' = Cys\text{—}Gly$$
$$LTE_4\ R' = Cys$$

By antagonizing the effects of $LTC_4$, $LTD_4$ and $LTE_4$ or other pharmacologically active mediators at the end organ, airway smooth muscle, the compounds and pharmaceutical compositions of the instant invention are valuable in the treatment of diseases in which leukotrienes are a factor, such as asthma.

DETAILED DESCRIPTION OF THE INVENTION

The compounds of this invention are represented by the general structural formula (I)

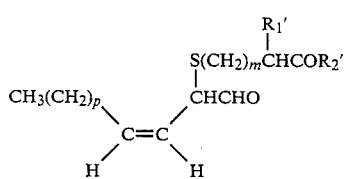

wherein m is 0, 1 or 2; p is 9, 10, 11, 12 or 13; $R_1'$ is hydrogen,

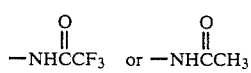

and $R_2'$ is amino, —$NHCH_2CO_2R_3'$,

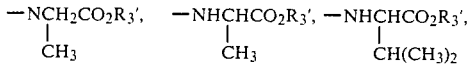

—$NHCH_2CONH_2$ or $OR_3'$ wherein $R_3'$ is an alkyl radical containing one to six carbon atoms with the proviso that when m is 0, $R_1'$ is hydrogen.

The compounds of formula (I) are chemical intermediates in the synthesis of leukotriene antagonists represented by the following general structural formula (II)

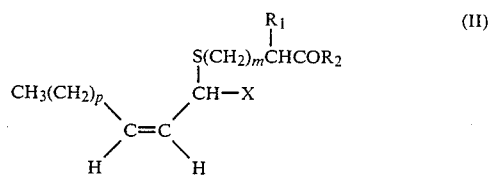

wherein m and p, are described above and $R_1$ is hydrogen, amino or

$R_2$ is hydroxyl, amino, —$NHCH_2CO_2H$,

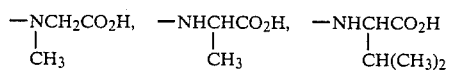

or —$NHCH_2CONH_2$; and X is

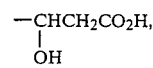

—$CO_2H$ or —$CH_2OH$. These leukotriene antagonists are the subject matter of co-pending applications Ser. No. 472,773 and Ser. No. 472,774.

Illustrative of the compounds of formula (I) are those compounds in which the alkyl group adjacent to the double bond contains 12 carbon atoms (i.e. p=11) which are represented by the general structural formula (III)

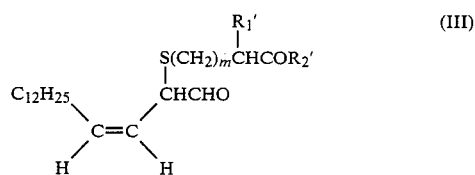

wherein m, $R_1'$ and $R_2'$ are described above.

The compounds of formula (III) are 3(Z)-hexadecenal derivatives and are exemplified by 2-[(2-carbomethoxyethyl)thio]-3(Z)l-hexadecen-1-al, wherein m is 1, $R_1'$ is hydrogen and $R_2'$ is methoxy.

The comounds of formula (I) are prepared via the following synthetic pathway starting from 4-hydroxybut-2(E)-en-1-al tetrahydropyranyl ether (1), wherein THP is a tetrahydropyranyl radical, as follows

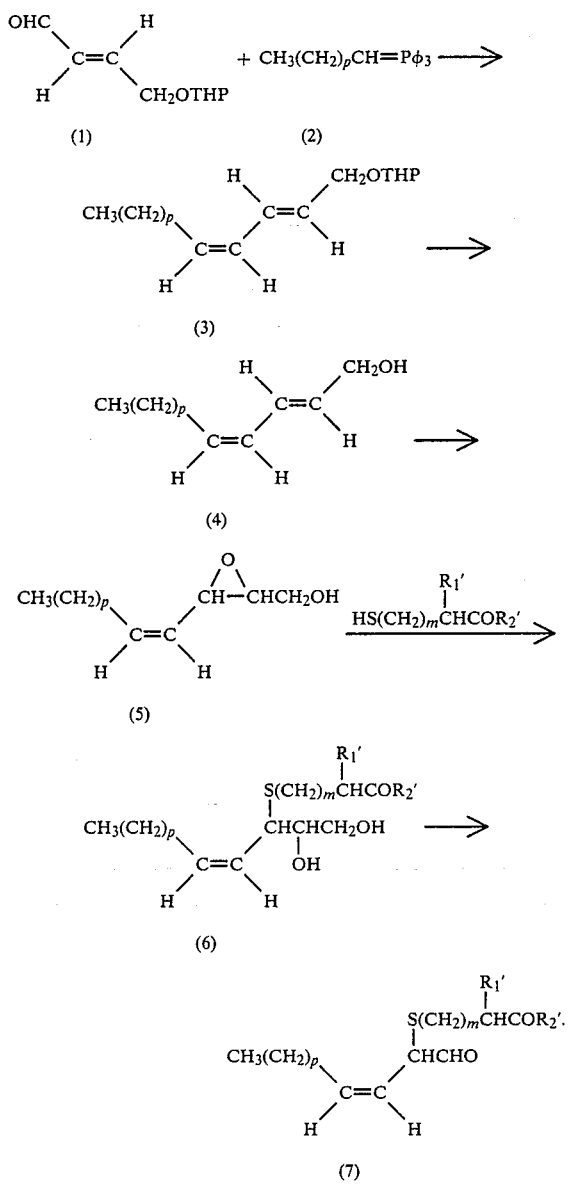

Compound 1, which is a known compound, is reacted with the appropriate alkyltriphenylphosphonium ylid under Wittig conditions to yield compound 3. Compound 3 is hydrolyzed to cleave the THP ether and gives compound 4 which is epoxidized to afford compound 5. Compound 5 is reacted with the appropriate mercaptan, wherein $R_1'$ and $R_2'$ are described above to give compound 6. Compound 6 is oxidatively cleaved to compound 7. Compound 7 is easily converted to the leukotriene antagonists of formula (II) through standard known chemical transformations.

The leukotriene antagonist activity of the compounds of formula (II) is measured by the ability of the compound to inhibit leukotriene induced contraction of guinea pig tracheal tissues in vitro. The following methodology was employed:

In vitro: Guinea pig (adult male albino Hartley strain) tracheal spiral strips of approximate dimensions 2 to 3 mm cross-sectional width and 3.5 cm length were bathed in modified Krebs buffer in jacketed 10 ml tissue bath and continously aerated with 95% $O_2$/5% $CO_2$. The tissues were connected via silk suture to force displacement transducers for recording isometric tension. The tissues were equilibrated for 1 hr., pretreated for 15 minutes with meclofenamic acid (1 μM) to remove intrinsic prostaglandin responses, and then pretreated for an additional 30 minutes with either the test compound or vehicle control. A cumulative concentration-response curve for $LTD_4$ on triplicate tissues was generated by successive increases in the bath concentration of the $LTD_4$. In order to minimize intertissue variability, the contractions elicited by $LTD_4$ were standardized as a percentage of the maximum response obtained to a reference agonist, carbachol (10 μM).

Calculations: The averages of the triplicate $LTD_4$ concentration-response curves both in the presence and absence of the test compound were plotted on log graph paper. The concentration of $LTD_4$ needed to elicit 30% of the contraction elicited by carbachol was measured and defined as the $EC_{30}$. The $pA_2$ value for the test compound as determined by the following equations:

$$\frac{EC_{30} \text{ (presence of test compound)}}{EC_{30} \text{ (presence of vehicle control)}} = \text{dose ratio} = X \quad 1.$$

$$K_B = \text{concentration of test compound}/(X - 1) \quad 2.$$
$$pA_2 \cong -\log K_B \quad 3.$$

The compounds of formula (II) possess biosignificant antagonist activity against leukotrienes, primarily leukotriene $D_4$. Representative of the antagonist activity of the compounds of formula (II), tabulated below are a number of claimed compounds and the $pA_2$ values calculated from the above test protocol

| Compound | $pA_2$ |
| --- | --- |
| 2[(2-carboxyethyl)thio]-3(Z)-hexadecenoic acid | 6.0 |
| 2[(2-carboxyethyl)thio]-3(Z) hexadecen-1-ol | 5.3 |
| 3-Hydroxy-4[(2-carboxyethyl)thio]-5(Z)-octadecenoic acid | 6.1 |

The following examples illustrate the preparation of the compounds of this invention and their conversion into known leukotriene antagonists and as such are not to be considered as limiting the invention set forth in the claims appended hereto.

EXAMPLE 1

Preparation of 2-[(2-carbomethoxyethyl)thio]-3(Z)-hexadecen-1-al [Formula (I) wherein m is 1; p is 11, $R_1'$ is hydrogen and $R_2'$ is methoxy]

(a) Heptadec-2(E),4(Z)-dienyl tetrahydropyranyl ether 1(a) (1) Heptadec-2(E),4(E) dienyl tetrahydropyranyl ether 1(a) (2)

Tridecyltriphenyl phosphonium bromide (189 g, 0.3 mole) was dissolved in 900 ml of tetrahydrofuran and cooled to 0° in an ice-salt bath while stirring under argon. A 2.2N solution of n-butyllithium in hexane (250 ml, 0.36 mole) was added dropwise over a period of 30 minutes. The mixture was stirred for an additional 20 minutes and then cooled to −70° in a dry ice-acetone bath. The 4-hydroxybut-2-(E)-en 1-al tetrahydropyranyl ether (51 g, 0.3 mole in 225 ml of tetrahydrofuran was added dropwise over a period of 35 minutes and the mixture stirred for an additional hour at −70°. The mixture was then poured into 6.25 liters of ether and stirred for 20 minutes. The resulting mixture was filtered through glass fiber filter paper. The filtrate was evaporated and the residue triturated with hexane, filtered and evaporated to give a ~3:1 mixture of 1(a) (1): 1(a) (2).

(b) Heptadec-2(E),4(Z)-dien-1-ol 1(b) (1)
Heptadec-2(E),4(E)-dien-1-ol 1(b) (2)

The mixture of compounds 1(a) (1) and 1(a) (2) (80 g, 0.24 mole) was dissolved in 3 liters of methanol and the -pyridinium p-toluenesulfonate acid (3 g, 0.012 mole) was added to the mixture stirring under argon at room temperature. The progress of the reaction was monitored by tlc. When the reaction was complete the solvent was evaporated and the residue flash chromatographed on 500 grams of silica gel eluted with 10% ethyl acetate in hexane to give 52 grams (87%) of a ~3:1 mixture of 1(b) (1): 1(b) (2). Separation of 1(b) (1) from 1(b) (2) was accomplished by careful chromatography on silica gel. Compound 1(b) (1) mp 34°–37°. Compound 1(b) (2) mp 51°–55°.

(c) Trans-2,3-epoxy-4(Z)-heptadecen-1-ol 1(c)

Compound 1(b) (1) (2.52 g, 10 mmol) was dissolved in 100 ml of methylene chloride stirring at room temperature under argon. A 0.5N solution of sodium bicarbonate (30 ml) was added. The 85% m-chloroperbenzoic acid (2.03 g, 10 mmol) was added slowly in small portions. The mixture was stirred for 1.5 hours after the addition was complete. The phases were separated and the aqueous phase washed with methylene chloride. The combined organic phases were dried over anhydrous sodium sulfate filtered and evaporated. The residue was flash chromatographed on 100 grams of silica gel eluted with 10–20% ethyl acetate-hexane to give compound 1(c).

(d)
3-[(2-Carbomethoxyethyl)thio]-4(Z)-heptadecen-1,2-diol 1(d)

Compound 1(c) (7.2 g, 26.9 mmol) was dissolved in 40.2 ml of methanol containing 2% triethylamine. This solution was stirred at room temperature under argon and a solution of methyl 3-mercaptopropionate (4.92 ml, 44.4 mmol) and triethylamine (11.16 ml, 80.2 mmol) in 40.2 ml of methanol was added dropwise over a period of 15 minutes. The mixture was stirred for 5 hours at room temperature and then placed in the refrigerator overnight. The solvents were evaporated and the residue flash chromatographed on 500 grams of silica gel eluted with 10–50%, ethyl acetate in hexane to give compound 1(d), mp. 33°–36°.

(e) 2-[(2-Carbomethoxyethyl)thio]-3(Z)-hexadecen-1-al 1(e)

Compound 1(d) (2 g, 5.15 mmol) was dissolved in 10 ml of diethyl ether and stirred in a room temperature water bath. A saturated solution (100 ml) of periodic acid in diethyl ether was added in a single portion. The resulting mixture was stirred for two minutes and then immediately flash chromatographed on 150 g of silica gel with 10% ethylacetate in hexane to give compound 1(e).

The following intermediate compounds are prepared by the general method of Example 1 by employing the appropriate thiol containing compound for methyl-3-mercaptopropionate:

2-[(carbomethoxymethyl)thio]-3(Z)-hexadecen-1-al;
2-[(3-carboethoxypropyl)thio]-3(Z)-hexadecen-1-al;
2-[(3-carbopropoxymethylamino-3-oxopropyl)thio]-3(Z)-hexadecen-1-al;
2-[(2-trifluoromethylamido-3-carbomethoxymethylamino-3-oxopropyl)thio]-3(Z)-hexadecen-1-al;
2-[[(aminocarbonyl)ethyl]thio]-3(Z)-hexadecen-1-al; and
2-[(2-acetamido-2-carboethoxyethyl)thio]-3(Z)-hexadecen-1-al.

Homologs of the above compounds are prepared by employing an appropriate alkyltriphenyl phosphonium bromide, such as undecyltriphenyl phosphonium bromide or pentadecyltriphenyl phosphonium bromide, in place of tridecyltriphenyl phosphonium bromide in Example 1(a).

EXAMPLE 2

Preparation of 2[(2-carboxyethyl)thio]-3(Z)-hexadecen-1-ol [Formula (II) wherein m is 1; p is 11; $R_1$ is hydrogen; $R_2$ is hydroxyl and X is —$CH_2OH$]

(a) 2-[(2-Carbomethoxyethyl)thio]-3(Z)-hexadecen-1-ol

Compound from Example 1(e) (192 mg, 0.5 mmol) was dissolved in 1 ml of methanol and stirred at 0° C. under argon. Sodium borohydride (38 mg, 1 mmol) was added and the mixture stirred at 0° C. for 5 minutes. The mixture was acidified with dilute hydrochloric acid and evaporated. The residue was taken up in diethyl ether and washed with dilute hydrochloric acid, aqueous sodium bicarbonate, dried over anhydrous sodium sulfate, filtered and evaporated to give crude product which was flash chromatographed on 20 grams of silica gel eluted with 15% ethylacetate in hexane to give the above-noted compound.

(b) 2-[(2-Carboxyethyl)thio]-3(Z)-hexadecen-1-ol

Compound from 2(a) (180 mg, 0.5 mmol) was dissolved in 1 ml of methanol and a 1N solution of sodium hydroxide (1 ml, 1 mmol) was added. The mixture was stirred at room temperature under argon for 3 hours and then placed in the freezer over the weekend after which time it was stirred for an additional 2 hours at room temperature until tlc indicated only a trace of starting material remained. The methanol was stripped off and the residue acidified with dilute hydrochloric acid and extracted with chloroform. The organic phase dried over anhydrous magnesium sulfate filtered and evaporated to give crude product. This was recrystallized from hexane at −78° C. to give the desired compound, mp 39°–40° C.

|   | Theory | Found |
| --- | --- | --- |
| C | 66.23 | 66.47 |
| H | 10.53 | 10.77 |
| S | 9.30 | 9.15 |

EXAMPLE 3

Preparation of 2-[(2-carboxyethyl)thio]-3(Z)-hexadecenoic acid [Formula (II) wherein m is 1, $R_1$ is hydrogen and $R_2$ is hydroxyl and X is —$CO_2H$]

(a) 2-[(2-Carbomethoxyethyl)thio]-3(Z)-hexadecenoic acid 3(a) (1) Methyl-2-[(2-carbomethoxyethyl)thio]-3(Z)-hexadecenoate 3(a) (2)

Compound from Example 2(a) (0.8 g, 2.25 mmol) was dissolved in 5.5 ml of acetone. The solution was cooled to −40° C. and stirred under argon. Jones reagent (0.3 ml, 0.6 mmol) was added and the mixture stirred between −30° and −40° C. for 30 minutes. Additional Jones reagent (0.3 ml, 0.6 mmol) was added and the mixture stirred for 1 hour. The remaining Jones reagent (0.145 ml, 0.29 mmol) was added. Thirty minutes later the reaction which had been maintained in a temperature range of −30° to −40° C. throughout the reaction was quenched by the addition of 1 ml of isopropanol. The solvents were stripped off and the residue partitioned between diethyl ether and $H_2O$. The aqueous phase was extracted with diethyl ether. The combined organic phases were dried over anhydrous $MgSO_4$ filtered and evaporated to give the crude product 3(a) (1). In order to facilitate purification, compound 3(a) (1) was treated with excess diazomethane in diethyl ether at 0° and allowed to warm to room temperature. The solvents were evaporated and the residue flash chromatographed on 200 grams of silica gel eluted with 5% EtOAc-hexane to give the desired product 3(a) (2).

(b) 2-[(2-Carboxyethyl)thio]-3(Z)-hexadecenoic acid

Compound 3(a) (2) (0.16 g, 0.41 mmol) was dissolved in 3.2 ml of methanol and stirred under argon at 0° C. A 1N solution of sodium hydroxide (1.6 ml, 1.6 mmol) was added and the ice bath removed. The mixture was stirred at room temperature for 2½ hours. The methanol was evaporated and the residue cooled in an ice bath and acidified with dilute HCl. The aqueous phase was extracted twice with diethyl ether. The combined ether extracts were dried over anhydrous sodium sulfate, filtered and evaporated to give crude product. This was recrystallized from diethyl ether-hexane to give the desired compound, mp 52°-54° C. Anal. Calcd. C: 63.65; H: 9.56; S: 8.94; Found C: 63.59; H: 9.45; S: 9.24.

EXAMPLE 4

Preparation of 3-Hydroxy-4-[(2-carboxyethyl)thio]5(Z)-octadecenoic acid [Formula (II) wherein m is 1; p is 11; $R_1$ is hydrogen; $R_2$ is hydroxyl and X is

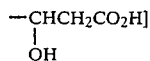

(a) Methyl 3-hydroxy-4-(carbomethoxyethylthio)5(Z)-octadecenoate 4(a)

A dry flask sealed with a septum and maintained under an argon atmosphere was charged with 4.5 ml of hexane and cooled in an ice bath. A 2.2M solution of n-BuLi (1.03 ml, 2.25 mmol) was added followed by the dropwise addition of diisopropyl amine (0.315 ml, 2.25 mmol). The solution was stirred at 0° for 10 minutes and then cooled to −78° in a dry ice-acetone bath for 15 minutes. A solution of methyl acetate (0.18 ml, 2.25 mmol) in 1.5 ml hexane was added over a period of 1 minute and the mixture stirred at −78° for an additional minute. The mixture at this time was almost clear. Compound 1(e) (750 mg, 2.1 mmol) in 1.5 ml of hexane was added over a period of 1 minute resulting in a clear yellow solution which was stirred at −78° for an additional 15 minutes. The reaction mixture was then flash chromatographed on 100 grams of silica gel eluted with 15% ethyl acetate in hexane to give compound 4(a).

(b) 3-Hydroxy-4-[(2-carboxyethyl)thio]-5(Z)-octadecenoic acid

Compound 4(a) (0.2 g, 0.46 mmol) was dissolved in 5 ml of methanol and stirred under an argon atmosphere at 0°. A 1N solution of sodium hydroxide (2 ml, 2 mmol) was added dropwise over a period of 0.5 minute. The ice bath was removed and the reaction allowed to warm to room temperature for 2 hours. Most of the methanol was evaporated and the aqueous residue was cooled in an ice bath and acidified with dilute hydrochloric acid. The aqueous phase was extracted twice with diethyl ether. The combined ether extracts were dried over anhydrous sodium sulfate, filtered, and evaporated to give crude product. This was recrystallized from diethyl ether-hexane to give the desired compound, mp 88°-97°. Anal. Calcd. C: 62.65; H: 9.51; S: 7.96; Found C: 62.32; H: 9.38; and S: 8.10.

What is claimed is:

1. A compound represented by the structural formula (I)

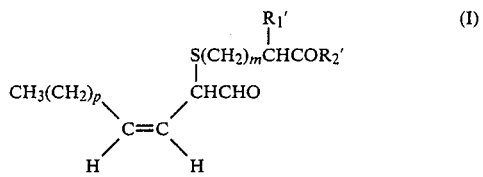

wherein m is 0, 1 or 2; p is 9, 10, 11, 12 or 13; $R_1'$ is hydrogen,

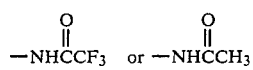

and $R_2'$ is amino, $-NHCH_2CO_2R_3'$,

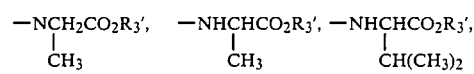

$-NHCH_2CONH_2$ or $-OR_3'$ wherein $R_3'$ is an alkyl radical containing one to six carbon atoms with the proviso that when m is 0, $R_1'$ is hydrogen.

2. A compound according to claim 1 wherein p is 11.

3. A compound according to claim 2 wherein m is 1, $R_1'$ is hydrogen and $R_2'$ is methoxy, designated 2-[(2-carbomethoxyethyl)thio]-3(Z)-hexadecen-1-al.

* * * * *

UNITED STATES PATENT AND TRADEMARK OFFICE
CERTIFICATE OF CORRECTION

PATENT NO. : 4,533,747

DATED : August 6, 1985

INVENTOR(S) : John G. Gleason, Ralph F. Hall and Thomas W. Ku

It is certified that error appears in the above-identified patent and that said Letters Patent is hereby corrected as shown below:

Abstract, in the definition of $R_2'$;

Column 2, lines 1-5; and

Claim 1, column 8, lines 50-55;

at each occurrence,

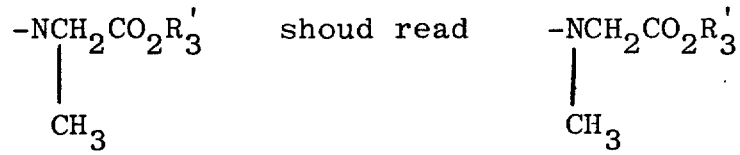

$$-\underset{\underset{CH_3}{|}}{N}CH_2CO_2R_3' \quad \text{shoud read} \quad -\underset{\underset{CH_3}{|}}{N}CH_2CO_2R_3'$$

Signed and Sealed this

Nineteenth Day of November 1985

[SEAL]

Attest:

DONALD J. QUIGG

Attesting Officer

Commissioner of Patents and Trademarks